United States Patent [19]
Ray et al.

[11] Patent Number: 5,172,420
[45] Date of Patent: Dec. 15, 1992

[54] METHOD FOR MONITORING THE DIMENSIONS AND OTHER ASPECTS LINEWIDTH THICKNESS AND DISCOLORATION OF SPECULAR PATTERNS

[75] Inventors: Rajarshi Ray, Princeton, N.J.; David R. Riese, Bradford, Mass.

[73] Assignee: AT&T Bell Laboratories, Murray Hill, N.J.

[21] Appl. No.: 884,857

[22] Filed: May 11, 1992

Related U.S. Application Data

[63] Continuation of Ser. No. 706,461, May 28, 1991, abandoned.

[51] Int. Cl.⁵ ............................................. G06K 9/00
[52] U.S. Cl. ..................................... 382/8; 358/106; 356/237; 382/55
[58] Field of Search .................. 302/8, 55; 358/106, 358/107; 356/237

[56] References Cited

U.S. PATENT DOCUMENTS

| | | | |
|---|---|---|---|
| 4,644,585 | 2/1987 | Crimmins et al. | 358/106 |
| 4,692,943 | 9/1987 | Pietzch et al. | 382/8 |
| 4,928,313 | 5/1990 | Leonard et al. | 382/8 |
| 4,975,972 | 12/1990 | Bose et al. | 382/8 |
| 5,046,113 | 9/1991 | Hoki | 358/106 |

OTHER PUBLICATIONS

A. J. Blodgett, "Microelectronic Packaging," *Scientific American*, vol. 247, pp. 86–96, Jul. 1983.

G. Dishon and O. Hecht, "Application of Automatic Optical Inspection (AOI) in the Manufacturing Technology of Thin Film Multichip Module (MCM)," *Proc. NEPCON West*, 12 pages, 1990.

*Primary Examiner*—Leo H. Boudreau
*Assistant Examiner*—David Foy
*Attorney, Agent, or Firm*—R. B. Levy

[57] ABSTRACT

Inspection of a metallized pattern (14) on a substrate (12) to monitor both the lateral dimensions and the intensity variation beyond tolerance limits is carried out by first capturing the image of the pattern with a television camera (20). The captured image is then compared to each of two models (40 and 42) comprising comparison patterns whose features have their lateral dimensions eroded and dilated, respectively, and the other aspect dilated and eroded, respectively, by a factor corresponding to the dimensional and intensity tolerances. The results of such comparison are logically combined to yield an image containing only defects (if any).

5 Claims, 2 Drawing Sheets

FIG. 1
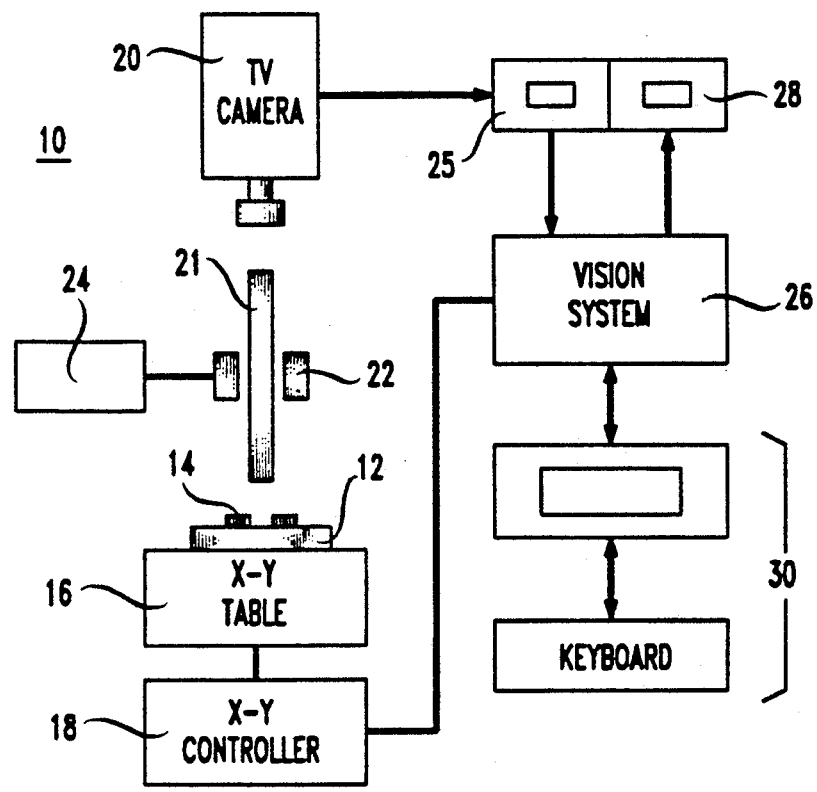
FIG. 2
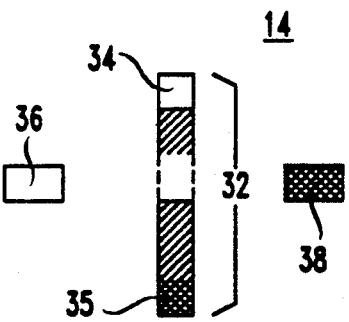
FIG. 3
| 51 | 50 | 50 | 38 | 39 | 50 | 50 | 48 |
|----|----|----|----|----|----|----|----|
| 50 | 49 | 50 | 14 | 16 | 50 | 49 | 48 |
| 51 | 40 | 40 | 49 | 48 | 16 | 12 | 13 |
| 51 | 50 | 48 | 14 | 14 | 50 | 51 | 48 |
| 50 | 51 | 51 | 12 | 12 | 50 | 50 | 50 |

FIG. 4
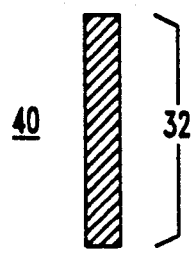
FIG. 5
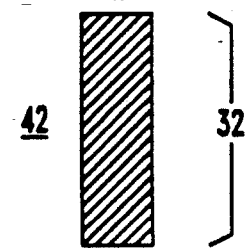
FIG. 6
| 51 | 50 | 50 | 50 | 18 | 49 | 48 | 49 |
|----|----|----|----|----|----|----|----|
| 50 | 50 | 50 | 50 | 16 | 50 | 49 | 50 |
| 50 | 50 | 50 | 50 | 17 | 50 | 49 | 50 |
| 51 | 51 | 51 | 51 | 17 | 49 | 48 | 49 |
| 50 | 51 | 51 | 51 | 18 | 50 | 50 | 50 |
FIG. 7
| 51 | 50 | 50 | 15 | 15 | 15 | 49 | 48 |
|----|----|----|----|----|----|----|----|
| 50 | 50 | 50 | 13 | 13 | 14 | 50 | 49 |
| 50 | 50 | 50 | 14 | 14 | 14 | 50 | 49 |
| 51 | 50 | 51 | 14 | 13 | 13 | 49 | 48 |
| 50 | 51 | 51 | 15 | 15 | 15 | 50 | 50 |
FIG. 8
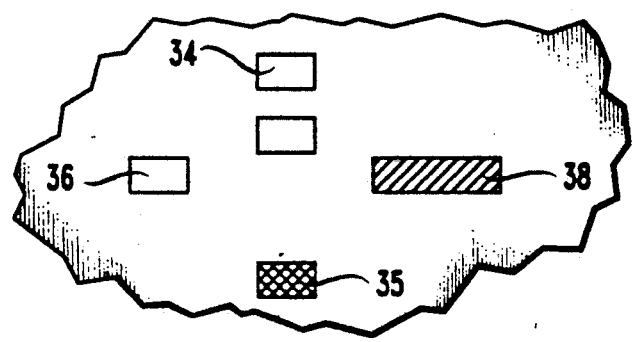

METHOD FOR MONITORING THE DIMENSIONS AND OTHER ASPECTS LINEWIDTH THICKNESS AND DISCOLORATION OF SPECULAR PATTERNS

This application is a continuation of application Ser. No. 706,461, filed on May 28, 1991, now abandoned.

TECHNICAL FIELD

This invention relates to a technique for monitoring both the lateral dimensions (e.g., linewidth) and at least one other aspect (e.g., intensity, hue, height, texture, reflectance, or saturation) of the features in a pattern of metallization on a substrate.

BACKGROUND OF THE INVENTION

Currently, much effort is being devoted to the development of multichip electronic modules. Such modules, also referred to by some as "Hybrid Integrated Circuits" (HICs), are typically comprised of a substrate, usually ceramic, which has one or more layers, each layer having a pattern of metallization thereon, usually gold or the like. Very Large Scale Integrated (VLSI) circuit chips are usually bonded to one or both of the major (i.e., outer) surfaces of the substrate, with each chip interconnected to another by the metallized pattern(s) on the substrate. Selected features of the metallized patterns on each layer of the substrate are connected to features on adjacent layers by through-plated metal vias.

To reduce the overall size of such multi-chip modules, as well as to allow for very dense circuits, the lateral dimensions of the pattern features (e.g., their linewidth) are made very small. On average, the linewidth of the features ranges from 2 to 10 mils, depending on the nature of the process employed to deposit the metallization on the substrate. Maintaining precise control of the dimensions of the features in each pattern is very important. If the dimensions of an individual feature in a pattern exceed the maximum allowable value under the operative design rule, the likelihood of leakage of a signal between such a feature and one adjacent to it becomes much higher, leading to possible "crosstalk." Conversely, if the lateral dimensions of a particular feature within a pattern are too small, then the impedance of the signal path provided by that feature may exceed permissible limits, adversely affecting the operation of the multi-chip module. Obviously, a break in a feature within a pattern is also undesirable. Further, the quality of such features as vias is also important.

Not only are the lateral dimensions of the features in each pattern on the substrate important, but the overall quality of the metallization in the pattern is also important. During the process of depositing the pattern on each layer of the substrate, it is possible for the metallization in the pattern to become contaminated. Such contamination not only adversely affects the impedance of the circuit paths established by the pattern, but may also adversely affect the ability to reliably bond an integrated circuit chip to the metallization on the exposed surfaces of the substrate. Another critical parameter is the uniformity of the height of the features in the pattern. Significant variations in the feature height can adversely affect the quality of the electrical connections made to devices placed on the substrate.

In the past, inspection of a metallized pattern on a substrate to detect undesirable lateral dimensional variations has been performed by comparing the image of the pattern (as captured by a television camera) to the image of each of a pair of master patterns or models. Such models are typically generated so each contains an exact replica of the desired pattern of features, except that the lateral dimensions of the features of one have been eroded (shrunk) while the lateral dimensions of the features of the other have been dilated (expanded) to represent the minimum and maximum allowable values, respectively. By comparing the image of the actual pattern of metallization to each of the two models and then logically combining the results of such comparison, those features whose dimensions are too large or too small can be detected.

While techniques, such as the one described above, have been devised for accomplishing automatic pattern inspection to detect deviations in the lateral dimensions of the features, no comparable methods have been devised for accomplishing automated inspection of both the lateral dimensions, as well as one or more other important aspects of the features, such as their height, hue, intensity, reflectance, texture, saturation or any combination thereof. If there is any inspection of any of these aspects, such inspection is carried out manually. For example, inspection of the intensity of the features to determine the pattern's hue and coloration is usually carried out manually and is subjective at best. Moreover, the results may be adversely affected by operator fatigue.

Thus, there is a need for a technique for accomplishing automated inspection of a pattern of metallization on a substrate to detect not only lateral dimensional variations, but variations associated with at least one other aspect of the feature.

SUMMARY OF THE INVENTION

Briefly, in accordance with the invention, a method is disclosed for inspecting a pattern on a substrate, such as a pattern of metallization on a multi-chip module, to monitor both the lateral dimensions and at least one other aspect of interest, such as reflectance, intensity, height, hue, texture, saturation or some combination thereof. The method is practiced by first capturing the gray-scale image of the pattern, typically with the aid of a television camera. Depending on the other aspect of interest, it may be necessary to further process the image to develop information about that aspect of interest. For example, if height is the other aspect of interest (beyond the x and y lateral dimensions of the features), it may be necessary to process the image of the pattern to develop a depth map thereof using known techniques.

Once the image is processed as necessary, the captured image is compared to a first and second model which contains an image of the pattern with the lateral dimensions of the features eroded and dilated, respectively, and the value of the other aspect of interest (e.g., intensity) dilated and eroded, respectively. The results obtained from such comparisons are logically combined and the results of such combination are used to establish whether the dimensions of the features and the aspect of interest (e.g., intensity) are within tolerance limits.

BRIEF DESCRIPTION OF THE DRAWING

FIG. 1 is a schematic block diagram of a system for monitoring both the lateral dimensions and at least one other aspect of interest of the features in a pattern of metallization on a substrate;

FIG. 2 is a graphical representation of an image of a specular pattern of metallization captured by the system of FIG. 1;

FIG. 3 is a map containing the values of the intensity of the image of FIG. 2;

FIGS. 4 and 5 each represent the image of a separate one of the first and second models used for comparison purposes with the image of FIG. 2;

FIGS. 6 and 7 each represent an intensity map of a separate one of the images of FIGS. 4 and 5, respectively, FIG. 8 depicts the representative image resulting from a logical combination of the intensity maps of FIGS. 3, 6 and 7.

DETAILED DESCRIPTION

FIG. 1 is a block schematic diagram of a system 10 for inspecting a substrate 12 containing a pattern of metallization 14. (For purposes of illustration, both the thickness of the substrate 12, and the pattern 14 of metallization thereon, have been exaggerated.) The system 10 comprises a x-y table 16 which serves to support the substrate 12 as well as to precisely displace it along both the x and y axes. The movement of the x-y table 16 is controlled by an x-y controller 18.

A television camera 20 is optically coupled through a microscope 21 trained on the x-y table 16 to capture the image of the substrate 12 and the pattern of metallization 14 thereon. Typically, the optics of the camera 20 and microscope 21 are such that only a small portion of the pattern 14 is within the field of view of the camera. As may be appreciated, by stepping the x-y table 16, different portions of the pattern 14 can be brought within the field of view of the camera 20. A ring lamp 22, powered by a light source 24, is provided to illuminate the upper surface of the substrate 12. Another lamp (not shown) may be provided to illuminate the undersurface of the substrate.

The output signal of the camera 20 is looped through a first television monitor 25 before being supplied to a vision system 26, which, in a preferred embodiment, comprises either an IRI Model P256 or P512 vision system, both available from IRI, Carlsbad, Calif. The vision system 26 serves to process the image of the camera 20 as well as to control the movement of the x-y table 16 by supplying control signals to the x-y controller 18. A second television monitor 28, identical to the monitor 25, is coupled to the output of the vision system 26 for displaying images produced thereby. The vision system 26 is typically programmed through a terminal 30.

As will be described in greater detail below, the vision system 26 serves to process the image captured by the camera 20 to determine if the lateral dimensions and at least one other aspect of the features (e.g., intensity, height, reflectance, texture, hue, saturation or combination thereof) of the pattern of metallization 14 on the substrate 12 are within tolerance limits. With the exception of the height of the pattern 14 features, the actual value of the other listed aspects can be obtained directly from the system 10. To obtain the height information, a system such as the one disclosed in U.S. patent application Ser. No. 440,948, filed Nov. 24, 1989, in the name of I. Amir and assigned to the same assignee herein, may be employed.

In the preferred embodiment, the system 10 is designed to monitor both the lateral dimensions of the pattern 14 as well as the intensity thereof. Referring to FIG. 2, there is shown an image captured by the camera 20 of FIG. 1 of a portion of the pattern of metallization 14. The portion of the metallized pattern 14 depicted in FIG. 2 includes a thin, broken stripe 32 having an excessively bright area 34 near the top of the figure and an excessively dark area 35 near the bottom of the figure. In addition to the broken stripe 34, the pattern 14 shown in FIG. 2 also includes an excessively bright, extraneous metallized area 36 to the left of the broken stripe 32 and an excessively dark, extraneous metallized area 38 to the right of the stripe. The excessively bright and dark areas 34 and 35 (as well as the areas 36 and 38) represent those areas within the portion of the pattern 14 of FIG. 1 whose intensity is outside an acceptable range, due, for example, to contamination of the metallization. Were the portion of the pattern of metallization 14 shown in FIG. 2 defect-free, the stripe 32 would be unbroken and of uniform intensity and the extraneous areas of metallization 36 and 38 would be absent.

When supplied with the output signal of the camera 20 of FIG. 1, the vision system 26 of FIG. 1 serves to establish the relative intensity of each of a plurality of small picture elements (pixels) which comprise the captured image shown in FIG. 2. FIG. 3 is a map of the intensity of the pixels within the image of FIG. 2, as measured on a scale of 0 to 255. As may be appreciated, the areas within the image of FIG. 2 which are free of any metallization generally have an intensity in FIG. 3 within the range of 48–51. The areas in FIG. 2 which are metallized (e.g., the areas comprising the stripe 32) have an intensity ranging from 12 to 40 in FIG. 3, the lower value representing an excessively dark area and the upper value representing a excessively bright area.

In accordance with the invention, lateral dimensional variations and/or variations in the intensity of the pattern of metallization 14 on the substrate 12 of FIG. 1, which are outside of prescribed tolerances, can be detected by first creating two models 40 and 42, as shown in FIGS. 4 and 5, respectively. The model 40 represents an acceptable, and preferably perfect, pattern of metallization 14 (i.e., an unbroken stripe 32) whose x and y dimensions have been eroded (shrunk), typically by 10%, while its reflective intensity has been dilated (expanded) by 10%. Note that the erosion in y is not shown in FIG. 4. Conversely, the model 42 represents an acceptable, and preferably perfect pattern of metallization 14 (i.e., an unbroken stripe 32) whose lateral dimensions have been dilated by 10% but whose reflectance intensity has been eroded by 10%. The 10% variation in linewidth and reflectance intensity in the models 40 and 42 of FIGS. 4 and 5, respectively, represents the maximum allowable lateral dimensional variation and intensity. Larger allowable tolerances would require that the lateral dimensional variation and intensity values in the models 40 and 42 be adjusted accordingly. It should be noted that the tolerance values for both x and y lateral dimensions as well as for the intensity need not be equal.

FIGS. 6 and 7 depict the pixel intensity maps corresponding to the models 40 and 42 of FIGS. 4 and 5, respectively. The areas in the models 40 and 42 of FIGS. 4 and 5, respectively, which appear dark and bright, correspond to the small and large intensity values, respectively, in FIGS. 6 and 7. The pixel intensity values in FIGS. 6 and 7 associated with actual areas of metallization (the stripe 32) differ by 10% from the corresponding intensity values for the stripe in FIG. 3. Since the models 40 and 42 of FIGS. 4 and 5, respectively, each represent an eroded and dilated, acceptable version of the pattern of metallization 14 of FIG. 2, no extraneous areas of metallization 36 and 38 (see FIG. 2) are present in either model.

At the outset of inspection, each of the models 40 and 42 of FIGS. 4 and 5, respectively, is entered to the machine vision system 26 of FIG. 1. The models 40 and 42 are typically entered by imaging an acceptable (preferably a defect-free) pattern of metallization 14, and storing the resultant pixel map in the vision system 26. The map is then manipulated to yield the maps shown in FIGS. 6 and 7, whose values are adjusted to effectively erode and dilate, respectively, the lateral dimensions and to effectively dilate and erode the intensity, respectively.

Once the intensity maps of FIG. 6 and 7 (representing the models 40 and 42, respectively) are established, actual inspection of the substrate 12 is carried out by capturing at least a portion of the pattern of metallization 14 with the camera 20 of FIG. 1. Thereafter, the pixel intensity map (see FIG. 3) of the captured image is established. After the pixel intensity map of the imaged portion of the pattern 14 of FIG. 1 is established, then the map is compared to each of the pixel intensity maps (see FIGS. 6 and 7) associated with the corresponding portions of the models 40 and 42, respectively.

Such comparison is carried out by logically combining the pixel intensity map of FIG. 3 (corresponding to actual or "run-time" image of FIG. 2) with the map of FIG. 6 (corresponding to the model 40 of FIG. 4) (by subtracting the latter from the former) and by logically combining the map of FIG. 7 (corresponding to the model 42 of FIG. 4) with the map of FIG. 3 by subtracting the latter from the former. The results of these separate operations are then logically combined (by adding the results) to yield a set of intensity values which correspond to those of the image illustrated in FIG. 8. (As indicated earlier, the pixel intensity is measured on a scale of 0-255, so when the result of the logical combination of combining the maps of FIGS. 3 and 6 with the maps of FIGS. 7 and 3 is negative, the result is made zero in accordance with the pixel measurement scale. All that appears in FIG. 8 are the areas 34 and 35, which are excessively bright and dark, in FIG. 2 respectively, and the areas 36 and 38 of extraneous metallization, which collectively represent the defects in the portion of the pattern 14 of metallization shown in FIG. 2. Note that if the portion of the pattern 14 of FIG. 2 were defect-free, then the image depicted in FIG. 8 would appear entirely bright (entirely empty).

The manner in which the results of the comparison of the intensity map of FIG. 3 to the maps of FIGS. 6 and 7 is carried out is dependent on the contrast between the metallized pattern 14 and its surrounding background. When the pattern 14 appears dark and the background bright, the results of the comparison are combined as described. In the opposite case, when the pattern 14 appears bright and the background dark, the intensity map of FIG. 7 is subtracted from the map of FIG. 3, and, by the same token, the map of FIG. 3 is subtracted from the map of FIG. 6.

The foregoing discloses a technique for monitoring both the lateral dimensional variation and the intensity of a pattern of metallization 14 on a substrate 12 by comparing the pattern to each of a pair of models 40 and 42 containing a master copy of the pattern with the lateral dimensions eroded and dilated, respectively, and the intensity dilated and eroded, respectively. Note that while the system of FIG. 1 has been described for monitoring the intensity as one of the aspects of the pattern of interest 14, in addition to the lateral dimensions of the pattern features, the same technique can be employed to monitor other aspects., In other words, to monitor any other aspect, such as height, reflectance, texture, hue, saturation or any combination thereof, two separate models, each similar to the models 40 and 42, are created by dilating and eroding the lateral dimensions and by dilating and eroding the value of the aspect to be monitored by the appropriate tolerance factor. The actual image of the pattern 14 would then be compared to these two models and the results of such comparison would then be combined as described to yield an image containing only the defects, if any.

It is to be understood that the above-described embodiments are merely illustrative of the principles of the invention. Various modifications and changes may be made thereto by those skilled in the art which will embody the principles of the invention and fall within the spirit and scope thereof.

We claim:

1. A method for inspecting a specular pattern on a substrate to monitor both the lateral dimensions and at least one other aspect of interest of the features in the pattern thereof, comprising the steps of:
   (a) capturing the actual image of the pattern;
   (b) comparing the captured image to a first model, representing an image of a comparison pattern with the value of said aspect of interest in said model dilated to a maximum allowable value and the lateral dimensions of its features eroded to a minimum allowable value;
   (c) comparing the captured image to a second model, representing an image of a comparison pattern with the value of said aspect of interest in said model eroded to a minimum allowable value and the lateral dimensions of its features dilated to a maximum allowable value;
   (d) logically combining the results obtained by comparing the captured image to each of the first and second models; and
   (e) establishing whether the lateral dimensions and said aspect of interest of the pattern are within prescribed tolerance values in accordance with the results of the comparison.

2. The method according to claim 1 wherein said aspect of interest is the intensity of the features of the pattern.

3. The method according to claim 1 wherein the results of the comparisons are logically combined by subtracting the captured image from that of the first model, then subtracting the second model from the captured image, and adding the results of such subtractions.

4. The method according to claim 1 wherein the first model is established by the steps of:
   capturing the image of a comparison pattern having features corresponding to features in the pattern on the substrate;
   eroding the lateral dimensions of the features in the captured image of the comparison pattern by an amount corresponding a minimum allowable value; and
   dilating the value of said aspect of interest of the features in the captured image of the comparison pattern by an amount corresponding to a maximum allowable value.

5. The method according to claim 1 wherein the second template is established by the steps of:
 capturing the image of a comparison pattern having features corresponding to features in the pattern on the substrate;
 dilating the lateral dimensions of the features in the captured image of the comparison pattern by an amount corresponding a maximum allowable value; and
 eroding the value of said aspect of interest of the features of the captured image of the comparison pattern by an amount corresponding to a minimum allowable value.

* * * * *